United States Patent [19]

Kishimoto et al.

[11] 4,252,536
[45] Feb. 24, 1981

[54] METHOD AND SYSTEM FOR MEASURING BLOOD COAGULATION TIME

[75] Inventors: Shinichi Kishimoto, Uji; Masahiro Yoshioka, Kyoto, both of Japan

[73] Assignee: Kabushiki Kaisha Kyoto Daiichi Kagaku, Kyoto, Japan

[21] Appl. No.: 957,927

[22] Filed: Nov. 6, 1978

[30] Foreign Application Priority Data

Nov. 12, 1977 [JP] Japan .............................. 52-135956

[51] Int. Cl.³ .......................................... G01N 33/86
[52] U.S. Cl. ................................... 23/230 B; 23/918; 356/39; 364/497; 422/73
[58] Field of Search ................ 23/230 B, 918; 422/73; 356/39; 364/497, 498; 346/33 ME

[56] References Cited

U.S. PATENT DOCUMENTS

| | | | |
|---|---|---|---|
| 3,458,287 | 7/1969 | Gross et al. | 422/73 X |
| 3,463,614 | 8/1969 | Leslie | 422/73 X |
| 3,593,568 | 7/1971 | Schmitz et al. | 23/918 |
| 4,125,327 | 11/1978 | Margolis | 23/230 B |

*Primary Examiner*—R. E. Serwin
*Attorney, Agent, or Firm*—Darby & Darby

[57] ABSTRACT

A blood coagulation time measuring method comprising irradiating a mixture of blood plasma and reagent with a beam of specified amount of light, detecting changes in the amount of light scattered by the mixture, converting the resulting scattered light output signals to digital form at specified time interval, feeding the digital data to a computer, computing the difference between each input value and the input value immediately adjacent thereto with respect to time and storing the results, and determining the time, prior to the time at which a maximum difference value is obtained, at which a computed difference value corresponding to $1/n$ of the maximum difference value is obtained. The time thus determined is the end point of the coagulation time. A system for practicing this method is also disclosed.

8 Claims, 4 Drawing Figures

METHOD AND SYSTEM FOR MEASURING BLOOD COAGULATION TIME

The present invention relates to a method and a system for optically automatically performing various blood coagulation tests with use of the blood plasma.

The blood, when flowing out of the blood vessel through which it is flowing at all times, promptly stops due to the functions of the vessel and platelets and to the activity of clotting factors. Basically the blood coagulation is interpreted as the phenomenon in which various clotting factors inherent in the blood plasma and in platelets act on each other and become active due to damage to or disorder of tissues or blood vessel, converting fibrinogen in the blood plasma to insoluble fibrin. In the deficiency or absence of one or more congenital or other clotting factors, therefore, it is likely that bleeding can not be stopped promptly or completely, so that it is very critical to check the blood for clotting ability, for example, prior to surgical operation.

The blood is generally tested for clotting ability with use of the blood plasma as well known as prothrombin time (PT) determination and thromboplastin time (PTT) determination which are each performed with use of a special reagent, based on the phenomenon that the reagent acts to deprive the plasma under test of flowability to gel the plasma. Stated more specifically, the clotting time is determined by mixing the reagent with the blood plasma to be tested and measuring the time that elapses before clot formation begins (i.e. end point) after the addition of the reagent. When tested for coagulation, normal blood plasmas which have all the essential clotting factors in the proper state coagulate substantially in a definite time, but abnormal blood plasmas in which a certain factor or some factors are deficient or absent will not clog at all or will afford a result indicating a lower clotting ability than the normal. Furthermore, prothrombin time determination and other test methods, when involving a special procedure, indicate to what extent a particular clotting factor is deficient and are therefore useful in the diagnosis and treatment of diseases such as hemophilia which are attributable to abnormal blood.

For the measurement of coagulation time which can be done basically by the use of a stop watch and the unaided eye, various apparatus are known. They include a system incorporating dynamic means for measuring the time required by a sample under test to gel (as disclosed in U.S. Pat. No. 3,635,678), an apparatus which determines the clotting time by optically detecting the decrease in transmissivity which takes place when the blood plasma to be tested starts to coagulate (as disclosed in U.S. Pat. No. 3,458,287), and another apparatus for determining the clotting time by optically detecting the increase in light scattering similarly taking place (as disclosed in U.S. Pat. No. 3,450,501).

These apparatus utilize changes in the physical properties of the blood plasma to be tested. Strictly speaking, such physical changes are brought about by the chemical change of the blood plasma in which the fibrinogen in the plasma is converted to fibrin by the essential clotting factors. Thus the PT or PTT value measured can be defined as the time that elapses before fibrin formation starts after the addition of the reagent.

Although various measuring techniques have heretofore been used based on different fibrin detecting principles, they are alike in utilizing the formation of fibrin. However, the accuracy of coagulation tests is dependent largely on the detecting method employed.

The visual method of determining the instant fibrin starts to form, namely the end point of clotting time measurement, is subject to inaccuracies and is difficult for unskilled persons to practice. The dynamic detecting method in which the test blood plasma is subjected to stress at all times during the test period will not be accurate in measuring the time required for the plasma to start to coagulate spontaneously. In fact, these methods are not fully reliable when there arises the necessity of accurately promptly measuring the clotting ability, for example, for the treatment of cerebral thrombosis, a kind of thrombi attributable to an abnormally high clotting function, which is very similar in symptoms to cerebral hemorrhage but which must be handled promptly in exactly opposite manner to the latter.

Accordingly optical detecting methods are widely employed at present, especially with use of an optical system for measuring the clotting time based on changes in transmissivity. However, changes or reductions in transmissivity due to the formation of fibrin are very small as will be described below and involve difficulties in determining the end point. In fact, satisfactory results still remain to be achieved despite the attempts so far made to accurately determine the end point with use of a differentiation circuit, secondary differentiation circuit or the like incorporated into the measuring circuit. In contrast, the formation of fibrin entails greater changes in light scattering which can be depicted on a graph for clotting time determination with greater ease than is the case with transmissivity, but difficulty is encountered in obtaining sufficient amount of light. Thus the latter method has found only limited use. Moreover, conventional measuring systems utilizing scattered light similarly involve difficulty in accurately determining the end point. This is a serious drawback in that the prothrombin time of normal blood plasma is as short as about 12 seconds and that differences of the order of several seconds will be interpreted to indicate a disorder. In addition to accurate measurements required, the measuring systems must be capable of testing samples efficiently in an event of emergency or when handling a large number of samples, but conventional systems which utilize changes in light scattering are not so designed.

Accordingly the main object of the present invention is to provide a method and an apparatus for measuring blood clotting time which uses scattered light involving marked changes in optical properties and which is capable of accurately efficiently determining the end point.

This invention will be described below in greater detail with reference to accompanying drawings, in which.

Before the detailed description of the method and system of this invention, description will first be given of the method generally used at present for optically measuring the clotting time with use of transmitted light, followed by the description of the method which utilizes scattered light and on which the present invention is based.

With methods and systems in which transmitted light is utilized, the clotting time is measured by adding a reagent to the blood plasma sample to be tested, actuating a timing device at the same time and halting the timing device upon detecting means detecting an apparent end point to determine the time that has elapsed. The end point is detected by detecting the change in light transmissivity of the plasma-reagent mixture resulting from formation of fibrin. Curve A in FIG. 1 indicates the light transmissivity of the mixture as measured with the lapse of time, thus merely showing changes in the light transmissivity with time. Thus Curve A per se in no way involves any chemical meaning, whereas it is empirically known that the point b indicates where fibrin starts to form. Accordingly such a curve, when obtained, will provide PT or PTT measurement. The portion a of the curve represents the stage in which the reaction between the blood plasma and the reagent, although proceeding, has not resulted in the formation of fibrin, the portion c indicating the stage in which fibrin is formed most markedly, the portion d indicating the stage in which the fibrinogen in the blood plasma has almost completely been converted to fibrin.

Figure 1:
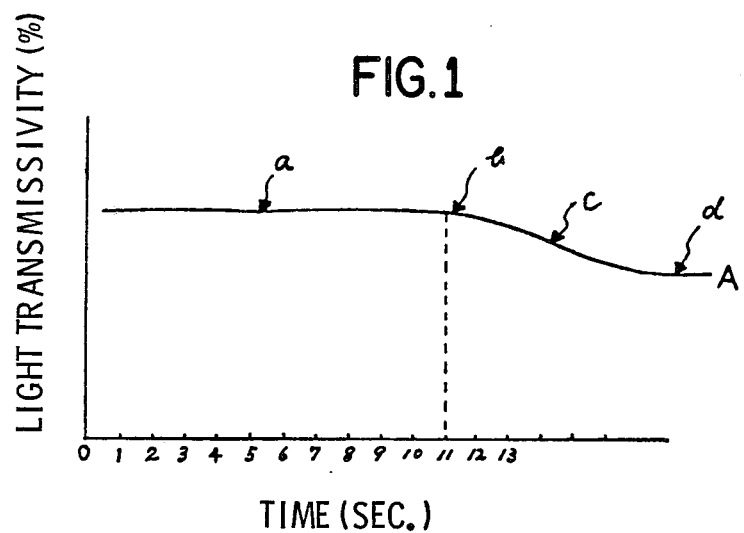
FIG. 1 is a diagram showing time-light transmissivity characteristics of a mixture of test blood plasma and reagent.

Curve A of FIG. 1 nevertheless is an ideal representation of the curve actually obtained; the actual curve shows, in the stage following the point b, smaller signal variations relative to the noise inherent in the system and therefore represents reduced variations, thus presenting difficulty in determining the end point. The situation becomes all the more serious when the blood plasma under test has an abnormal clotting factor. This indicates that the method of detecting changes in light transmissivity still remains to be improved in sensitivity. Additionally since the end point is determined simply by the first bent portion of Curve A, the measured value will invariably involve a range of variations. To overcome this drawback, various systems and methods have been provided for accurately detecting the time corresponding to the point b as by a differentiation circuit, secondary differentiation circuit, etc. incorporated in the measuring circuit, but the attempts heretofore made have not achieved satisfactory results as already stated.

Figure 2:
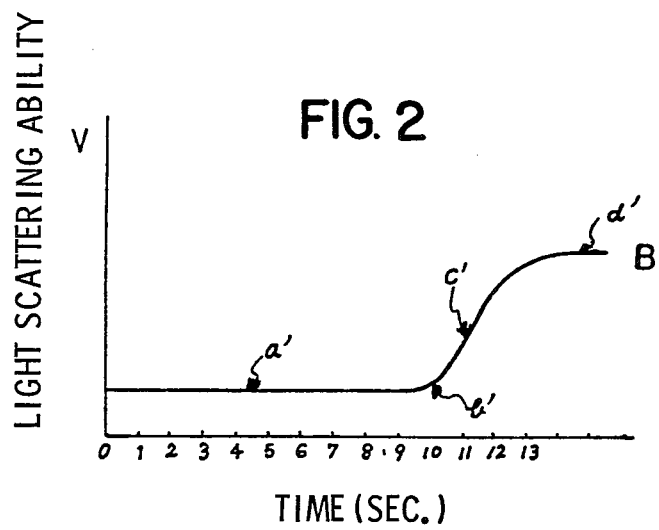
FIG. 2 is a diagram showing the time-light scattering ability characteristics of the same.

The present invention similarly provides an optically detecting method which, however, utilizes scattered light unlike most of the conventional methods which utilize transmitted light. The method of this invention determines the end point more efficiently with higher sensitivity than heretofore possible. The coagulated blood plasma which is used for PT or PTT determinations is usually in the form of a slightly turbid agar and has light transmissivity which is not much lower than that of the plasma before coagulation, whereas similar comparison in respect of light scattering reveals a very distinct difference as shown in FIG. 2. Based on this fact, this invention has been accomplished with the expediency to be described below.

FIG. 2 shows the light scattering ability of a blood plasma with the lapse of time in the course of PT determination. The reagent is added at 0 (sec.) on the time axis. Curve B of FIG. 2, although a somewhat idealized representation like FIG. 1, shows that the clotting time can be determined much more advantageously by the detection of changes in the intensity of scattered light than by the detection of changes in light transmissivity.

The portions a', b', c' and d' in FIG. 2 correspond to the portions a, b, c and d in FIG. 1.

This invention provides a system for detecting scattered light for PT and PTT determinations and also a method of effectively determining the end point. The principle on which the end point is determined according to this invention will be described with reference to FIG. 3.

Figure 3:
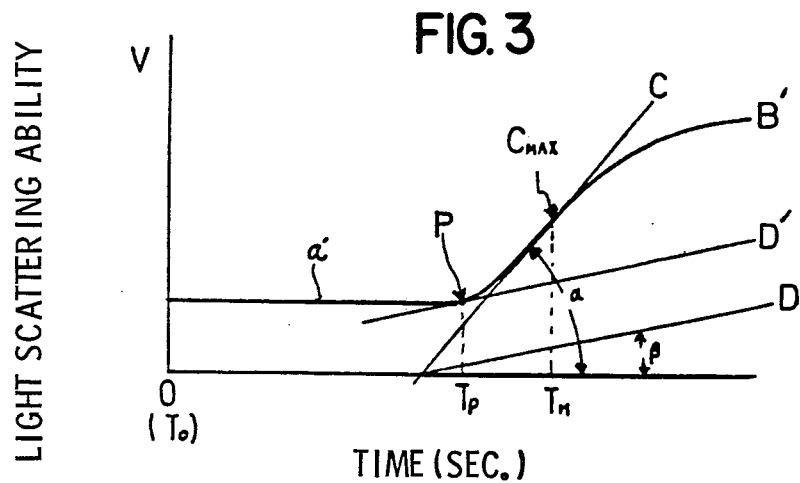
FIG. 3 is a diagram illustrating the principle of the method of the present invention.

Curve B' in FIG. 3, like Curve B in FIG. 2, represents variations in the intensity of light scattered by a test blood plasma as measured with the lapse of time, for example, for PT determination. Curve B' has a point $C_{MAX}$ at which the intensity of scattered light increases at the highest rate. The point $C_{MAX}$ can be interpreted to be the point where fibrin is formed at the highest velocity. Straight Line C tangent to Curve B' at the point $C_{MAX}$ is drawn, and Straight Line D is then drawn at a slope ($\tan \alpha$) one-fourth the slope ($\tan \alpha$) of Straight Line C. Straight Line D' tangent to Curve B' is drawn in parallel to Line D to determine the point P where the Line D' is tangent to Curve B'. The position $T_P$ of the tangent point P on the time axis is very proximate to the point where Curve B' starts to rise in any actual case and can therefore be regarded as the end point. Although $\tan \beta$ is taken as $\frac{1}{4}$ of $\tan \alpha$ as an example, $\tan \beta$ may generally be $1/n$ where n is 2, 3, 5 or the like without resulting in any substantial change. However, if n is close to 1, Line D' approaches Line C, hence meaningless, whereas if n increases to excess, Line D' approaches the time axis in parallel thereto, failing to specify the point P. Thus n should actually be in the range of from 2 to 5.

The end point thus determined is more accurately approximate to the point of initiation of fibrin formation than the end point determined by any of the known methods and will not involve errors even when Curve B' slopes very gently due to an abnormal clotting factor.

The principle on which the end point is determined according to this invention has been described with reference to a diagram showing variations in the intensity or amount of scattered light as measured with the lapse of time. Curve B' is obtained by measuring the amounts of light scattered by the test blood plasma-reagent mixture by a light detector and recording the results on a recorder as converted to electric signals. According to this invention, the electric signals are further converted by analog-digital converter into digital data, which is processed by computer, a microcomputer or like operation means to determine the end point.

A measuring start instruction is first given to the computer as by a switch to set the time to $T_0$, in i.e. 0 (in FIG. 3). The scattered light signals in the digital form (FIG. 4, F) are fed to the computer at equal, i.e. specified, time interval. Good results are available with the cycle of signal input set, for example, at about 10 m. sec. The computer calculates the difference between two values of input data which are adjacent to each other with respect to time, and successively stores the results in memory. The computer observes progressive increase of the calculated differences to a maximum and the subsequent decrease, and when the maximum value (at time = $T_M$ in FIG. 3) is detected, the feed of input to the computer is discontinued. Subsequently the address of the memory storing the value corresponding to $\frac{1}{4}$ the maximum value is located. The value $\frac{1}{4}$ may alternatively be $\frac{1}{2}$ or $\frac{1}{3}$ as already stated. Since the data is stored in the memory at equal time interval, the address of the memory can also indicate the time. The time indicated by the memory address is of the same meaning as the time $T_P$ indicating the end point.

As is well known, the operation described before can be practiced by a computer and is easily programmable in several ways. However, nothing prior to the disclosure of this invention has revealed that blood coagulation tests can be accurately performed by the combination of the techniques described.

Figure 4:
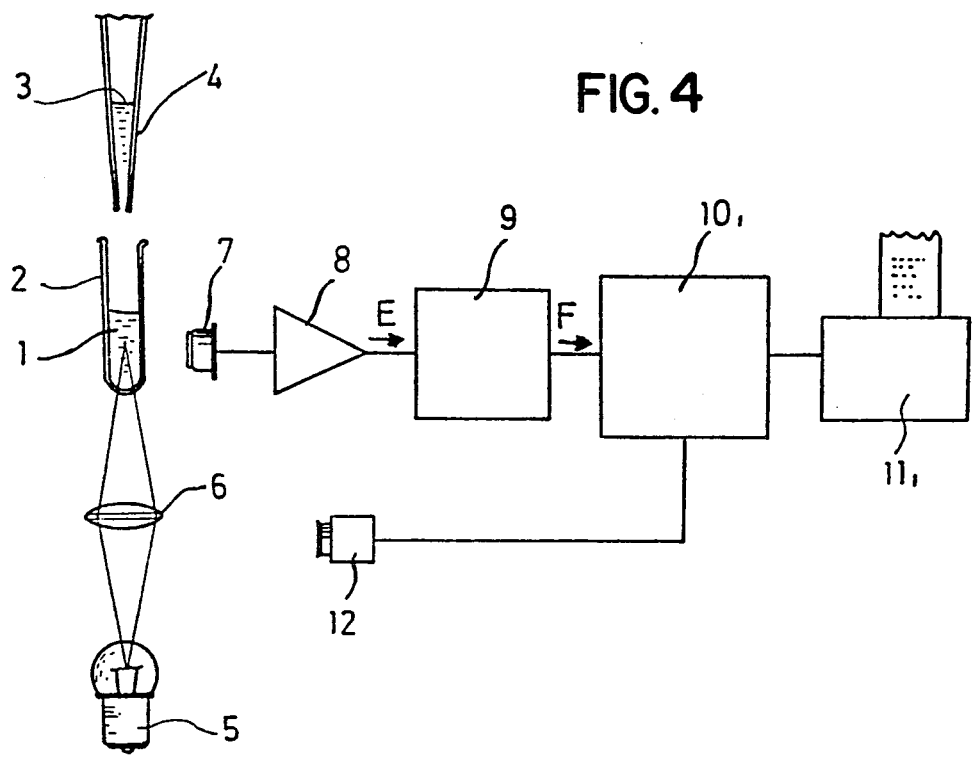
FIG. 4 is a block diagram showing a blood clotting time measuring system according to the invention.

The blood coagulation time measuring system of this invention will be described below in greater detail with reference to the FIG. 4 which is a block diagram showing the system. A pipette 4 containing a reagent 3 is disposed above a cell 2 containing a mixture 1 of the blood plasma to be tested and the reagent. Provided below the cell are a light source lamp 5 and a condenser lens 6 serving as means for projecting a beam of specified light amount onto the mixture 1 in the cell 2. On one side of the cell 2 there is provided a light detector 7 for measuring the amount of light scattered by the mixture 1 and converting the result to an electric signal. The scattered light output signal from the light detector 7 is amplified by a signal amplifier 8 and thereafter fed to an analog-digital converter 9, by which the amplified signal is converted to digital data. The signal from the analog-digital converter 9 is fed to and processed by a computer $10_1$ serving as operation means 10, and the result is printed out by a printer $11_1$ serving as output means 11.

The rays emitted from the light source lamp 5 are made into a beam of specified light amount by the condenser lens 6. The beam passes through the bottom of the cell 2 and irradiates the mixture 1 within the cell 2, with the result that part of the light is scattered by the mixture 1 and impinges on the light detector 7. A tungsten lamp or the like is usable as the lamp 5. When a light source for giving off a stabilized beam of specified light amount is used, the condenser lens 6 can be dispensed with. The light detector 7 may be a photoelectric tube, photocell or any other means which is capable of converting light to electric signals. Useful as the cell 2 is a test tube or some other bottomed cylindrical tube of transparent material, which is preferably of uniform shape and flawless as is desired for the measurement of the amount of scattered light. Although the light detector 7 in the present embodiment is disposed at 90 degrees with respect to the optical axis of the light emitted from the light source 5, the position of the detector 7 is not limited to a particular angle.

The light detector 7 continuously produces electric signals, which are amplified by the amplifier 8 to scattered light output signals E. The signals E are fed to the analog-digital converter 9, which gives off digital signals F as sampled at a specified time interval. The signals F are applied to the computer $10_1$ at the same time interval.

The computer $10_1$ processes the digital signals F by computing the difference between each input value and the input value immediately adjacent thereto with respect to time, and stores the results in the memory. Subsequently the computer determines the time ($T_P$ in FIG. 3), prior to the time ($T_M$ in FIG. 3) at which a maximum difference value is obtained, at which a computed difference value corresponding to 1/n of the maximum difference value is obtained, n being a number of about 2 to about 5 predetermined or optionally selected in accordance with PT, PTT or like test method concerned. The result is fed to the output means $11_1$ and printed out. Indicated at 12 in FIG. 4 is a measuring start switch.

The computer used as the operation means 10 in the embodiment described above may be a microcomputer to render the system compact. A computer of any scale is usable without departing from the basic feature of the invention. Alternatively a specific operation control circuit may be designed with use of a CPU composed of integrated circuits and introduced into wide use in recent years.

The measuring start switch 12 for the operation means may be a switch attached to the pipette and operatively related to the pipette when the pipette operates to place the reagent 3 into the cell 2, whereby the measuring operation can be initiated by a single action. The output means 11 can be a device for indicating the test result in digital form.

The method of measuring blood coagulation time according to this invention utilizes changes in the amount of light scattered by a mixture of the blood plasma to be tested and a reagent and is therefore featured by high detecting sensitivity, thus ensuring accurate PT and PTT measurements even when the test blood plasma contains a very small amount of fibrinogen. The end point is determined by continuously measuring changes in the amount of scattered light immediately after the mixture of the plasma and reagent in terms of electric signals, converting the signals to digital form and processing the digital data by difference calculation and subsequent specified operation, so that the end point of the coagulation time can be determined with high accuracy without involving errors that would result if the test is conducted by different persons or with use of different devices.

The system for measuring blood coagulation time according to the foregoing method of the invention is very simple to operate and is adapted to efficiently accurately conduct various blood coagulation tests with use of reagents.

What is claimed is:

1. A method for measuring the end point of blood coagulation time comprising the steps of
   providing a mixture of a blood sample and a reagent, irradiating the mixture with light.
   detecting the amount of light scattered from the irradiated mixture and producing an electrical signal representative thereof, and
   determining from said electrical signal a first time at which the most rapid change in the electrical signal is occurring and then determining as the end point at a time prior to said first time the time at which a change which is 1/n that of the most rapid change occurred, where n is greater than 1.

2. A method as in claim 1 wherein the step of detecting further comprises converting said electrical signal into digital signals at successive time intervals and storing the digital signals at succesive time intervals and storing the digital signals,
   and the step of determining comprises comparing successively stored digital signals to determine the maximum difference between two successively stored digital signals as said first time at which the most rapid change is taking place.

3. A method as in claim 1 wherein n is an integer of 2 or more.

4. A system for measuring the end point of blood coagulation time comprising:

a cell for containing a mixture of blood plasma and a reagent, means for irradiating the mixture with an amount of light, means for detecting the amount of light scattered by the irradiated mixture and producing an electrical output signal representative thereof, means for measuring at predetermined times the rate of change of said output signal corresponding to the rate of change of the scattered light, means for determining a first time at which the maximum rate of change of the output signal takes place and for determining as the end point of the coagulation a time prior to said first time at which the rate of change of the output signal is 1/n that of the maximum rate of change, where n is greater than 1.

5. A system as in claim 4 where n is an integer in the range of 2 to 5.

6. A system as in claim 4 wherein said measuring means comprises means for converting said output signal at said predetermined times into digital signals, means for storing said digital signals, said determining means comparing successive stored digitial signals to determine said first time.

7. A system as in claim 6 wherein said determining means includes means for determining from the stored digital signals the time when the rate of change of the output signal is 1/n that of the maximum rate.

8. A system as in claim 4 further comprising switch means operatively related to said cell for starting the measuring upon placing the reagent into the cell.

* * * * *